United States Patent [19]
Holmberg et al.

[11] Patent Number: 5,607,413
[45] Date of Patent: Mar. 4, 1997

[54] CONVEX OSTOMY FACEPLATE WITH FLOATING FLANGE AND FINGER RECESS

[75] Inventors: Steen Holmberg, Helsingor; Joergen F. Larsen, Skaevinge, both of Denmark

[73] Assignee: Dansac A/S, Fredensborg, Denmark

[21] Appl. No.: 615,038

[22] Filed: Mar. 12, 1996

[51] Int. Cl.[6] .................................................. A61F 5/44
[52] U.S. Cl. ......................... 604/342; 604/332; 604/338
[58] Field of Search ...................................... 604/332–345

[56] References Cited

U.S. PATENT DOCUMENTS

| | | | |
|---|---|---|---|
| 4,419,100 | 12/1983 | Alexander | 604/339 |
| 4,710,182 | 12/1987 | Bryson | 604/339 |
| 4,834,731 | 5/1989 | Nowak et al. | 604/339 |
| 4,973,323 | 11/1990 | Kaczmarek et al. | 604/339 |
| 5,316,607 | 5/1994 | Johnsen et al. | 156/212 |
| 5,501,678 | 3/1996 | Olsen | 604/344 |

*Primary Examiner*—Robert A. H. Clarke
*Attorney, Agent, or Firm*—Tilton Fallon Lungmus

[57] ABSTRACT

An adhesive faceplate for detachable connection to an ostomy pouch is disclosed. The faceplate has an integrated convex pressure ring for promoting stomal protrusion and a so-called floating flange (i.e., coupling ring) for mechanical attachment to the mating coupling ring of an ostomy pouch. The convex pressure ring is provided with a deep annular recess behind the faceplate's coupling ring to accommodate a user's fingers during a coupling operation, thereby facilitating attachment of a pouch. The pressure ring also includes a thin, inwardly-extending connecting portion which is heat sealed to the backing layer of the faceplate's adhesive wafer and, when that backing layer is formed of a porous material, such heat seal effectively closes the pores of the backing layer in the area of the seal.

8 Claims, 1 Drawing Sheet

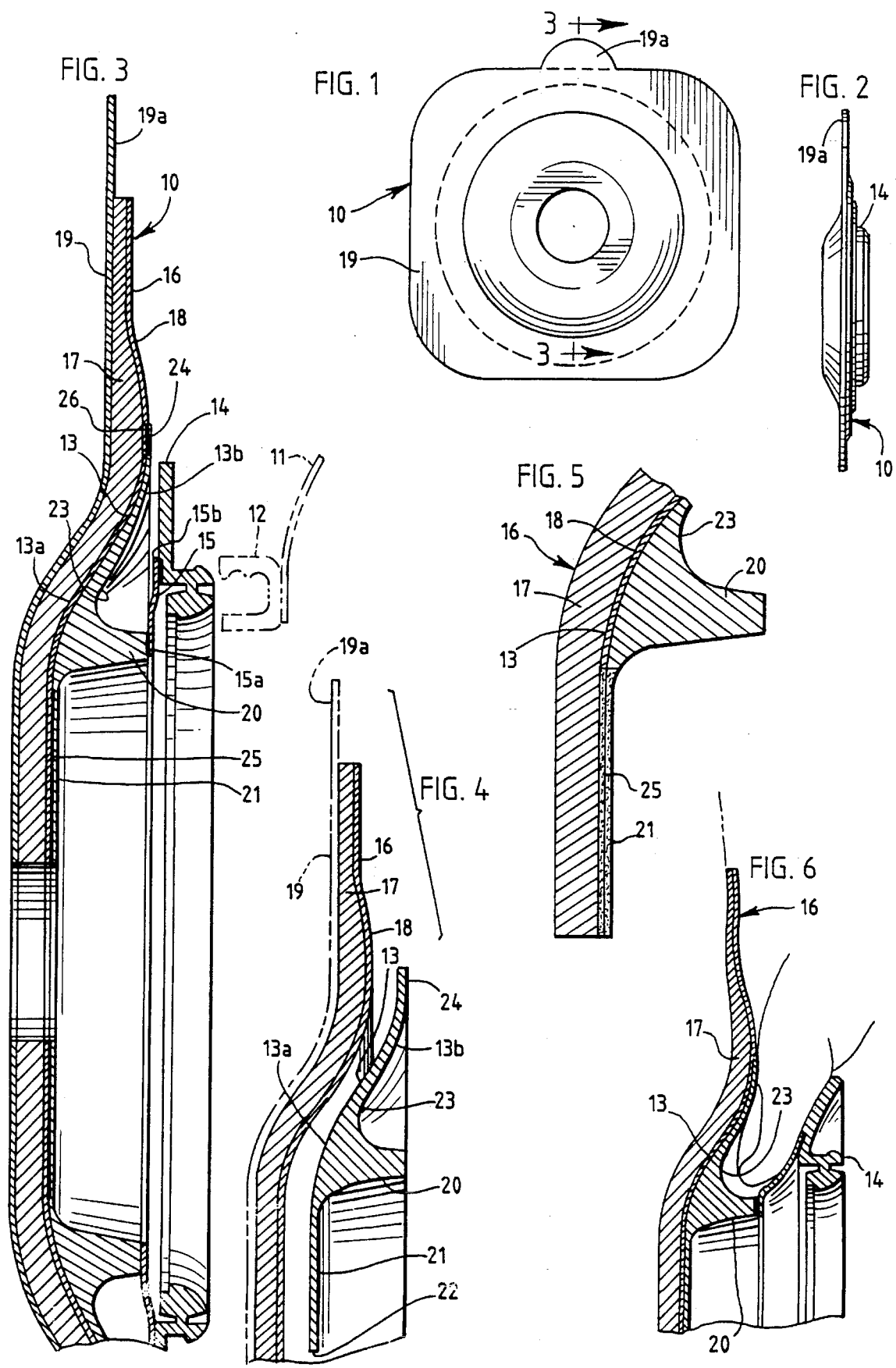

CONVEX OSTOMY FACEPLATE WITH FLOATING FLANGE AND FINGER RECESS

BACKGROUND AND SUMMARY

Ostomy Applicances having integrated convex pressure rings for promoting stomal protrusion are well known as disclosed, for example, in U.S. Pat. Nos. 4,973,323, 5,316,607, 4,834,731, 4,710,182, and International published application WO95/24169. It is also known to provide two-piece appliances with faceplates that have so-called floating flanges—that is, flanges or coupling rings that are mounted for limited movement towards and away from adhesive wafer components of the faceplates (see U.S. Pat. No. 4,419,100). However, efforts to combine the floating flange feature and convex pressure ring feature into a single faceplate, as disclosed in U.S. Pat. No. 4,834,731, have tended to result in relatively complex constructions having multiple layers, plural seals, and requiring numerous manufacturing steps.

A main aspect of this invention lies in providing a relatively simple but highly effective faceplate construction which has both a floating flange and a convex pressure ring, and in which the convex pressure ring contributes significantly in promoting ease of operation of the floating flange. To that end, the pressure ring is provided on its distal or pouch-facing side with an axially-extending mounting rib. The end of rib is joined to the inner edge of a thin annular web, and the outer edge of the web is sealed to the faceplate's coupling ring. The pressure ring has a deep annular recess located directly behind the coupling ring, making it easy for a user to insert his/her fingers behind the coupling ring (i.e., between the coupling ring and the remainder of the faceplate) during a coupling operation. The recess also has the effect of reducing the weight of the faceplate and rendering the pressure ring more flexible and conformable in use than it would be if the recess were absent. At the same time, the pressure ring provides the faceplate with sufficient convexity and stiffness to press against the peristomal skin surfaces and promote stomal protrusion when the appliance is worn.

The bodyside surface of the pressure ring is convex and is secured to the backing layer of an adhesive wafer. Preferably, the pliant adhesive material of the wafer has particles of one or more hydrocolloids dispersed therein and may be any of a variety of adhesive formulations generally known as skin barrier compositions. Ideally, the backing layer is both porous and thermoplastic. Although the backing layer extends inwardly all of the way to the stoma opening of the faceplate, the danger of fluids wicking outwardly through the pores of the film or fabric is avoided because of an extended heat seal between the backing layer and a thin, flexible inner portion of the pressure ring. The fusion between the backing layer and pressure ring in the area of the annular heat seal obliterates the pores of the backing layer in that area, thereby closing off routes that might otherwise exist for the outward migration of fluids when the appliance is used.

Other features, advantages and objects will become apparent from the specification and drawings.

DRAWINGS

FIG. 1 is a plan view of a faceplate embodying the invention.

FIG. 2 is a side elevational view of the faceplate.

FIG. 3 is an enlarged cross sectional view taken along line 3—3 of FIG. 1.

FIG. 4 is a fragmentary sectional view showing the wafer and pressure ring in unconnected condition.

FIG. 5 is an enlarged fragmentary sectional view depicting the heat seal between the pressure ring and wafer.

FIG. 6 is a sectional view similar to FIG. 3 but showing use of the finger recess when the faceplate is to be connected to a pouch.

DETAILED DESCRIPTION OF PREFERRED EMBODIMENT

Referring to the drawings, the numeral 10 generally designates the faceplate of a two-piece ostomy appliance. The other component of the appliance is a conventional pouch 11 with a coupling ring 12 indicated in phantom in FIG. 3. Since the pouch component does not constitute any part of this invention, further description is believed unnecessary herein. However, reference may be had to U.S. Pat. No. 5,185,008 for details of the coupling system shown herein.

The faceplate 10 comprises a convex pressure ring 13, a faceplate coupling ring 14, a connecting web 15, and an adhesive wafer 16.

The adhesive wafer consists essentially of two layers: a bodyside adhesive layer 17 and a pouchside backing layer 18 (FIG. 4). A third layer in the form of a release sheet 19 is also provided to protect the bodyside surface of the adhesive layer prior to use. Release sheet 19 may be formed of any suitable thermoformable plastic that is formulated or treated for allowing it to be easily peeled from the bodyside surface of adhesive layer 17. Most advantageously, the release sheet 19 is formed in one piece so that it may be removed in its entirety in one peeling step and, to facilitate such removal, a tab 19a projects outwardly beyond the edge of the adhesive layer as shown most clearly in FIGS. 1–4.

The adhesive layer may be composed of any adhesive suitable for attaching the faceplate to the peristomal skin surfaces of a patient. Particularly effective results have been achieved with skin-friendly adhesives, commonly known as skin barrier materials, that have both wet and dry tack and contain hydrocolloids capable of absorbing fluids and swelling as they do so. The hydrocolloid particles, which may consist of carboxymethylcellulose, pectin, gelatin, karaya, or any other of a variety of hydrocolloids and superabsorbents known for use in skin barrier formulations, are dispersed in a soft, pliant elastomeric adhesive material such as, for example, polyisobutylene.

Backing layer 18 may be of thin, flexible, thermoplastic film or foam; however, it is especially desirable that it be composed of a porous thermoplastic film or fabric. Particularly effective results have been obtained using a perforated polyethylene film that has a fabric-like texture, but other soft breathable or non-breathable thermoplastic materials may be used.

The convex pressure ring 13 has a convex bodyside surface 13a and a pouchside surface 13b from which an annular integral attachment rib 20 projects (FIG. 4). The pressure ring has a thin flexible inner connecting portion 21 that extends radially inwardly from the rib and terminates in a stoma-receiving opening 22.

Outboard of the rib 20 on the pouchside surface of the ring is a deep annular finger-receiving recess 23. The pressure ring continues outwardly, terminating in an outer connecting portion 24 that lies in substantially the same plane as the end of rib 20 (FIG. 4).

The inner connecting portion 21 is heat sealed to the thermoplastic backing layer 18 of the wafer 16 for the full radial extent of the inner connecting portion, as shown most clearly in FIG. 5. In the heat seal zone 25, the pressure ring and backing layer are fused together in a way that obliterates the pores of the backing layer when that backing layer is formed of a microporous material. The heat seal therefore not only secures the parts together but does so in a way that prevents the wicking or outward migration of fluids from about the stoma when the faceplate is worn.

It is important that the inner connecting portion 21 of the pressure ring be thin and flexible. When heat welded to the backing layer 18, the backing layer and inner connecting portion should have a combined thickness no greater than about 1.5 mm and, preferably, no greater than 0.8 mm. As a result, the pressure ring and wafer maintain flexibility inboard of rib 20 and are sufficiently thin as to be easily cut (with scissors) to enlarge the stoma-receiving opening of the faceplate when the appliance is being fitted on a patient.

As shown most clearly in FIG. 3, the outer connecting portion 24 of the pressure ring is heat sealed to the thermoplastic backing layer 18 of the wafer along annular heat seal zone 26.

The thermoplastic coupling ring 14 shown in the drawings is similar in construction and operation to the ring shown and described in U.S. Pat. No. 5,185,008, the disclosure of which is incorporated by reference herein. It is to be understood, however, that coupling rings of other mechanical constructions might be used. In any case, it is essential that the diameter of the coupling ring 14 be greater than the diameter of rib 20. A thin, flexible, imperforate annular web 15 joins the two, with the inner edge 15a of the web being heat sealed to the end of the rib 20 and its outer edge 15b heat sealed to coupling ring 14.

When the parts are so connected, web 15 and coupling ring 14 are aligned directly with finger-receiving recess 23. This allows the coupling ring to be urged away from the remainder of the faceplate simply by inserting a finger into the recess 23 as depicted in FIG. 6. When the coupling ring is so displaced, it may be easily joined to the mating ring 12 of a pouch simply by squeezing the two rings together between opposing fingers. The coupling rings are therefore joined together with far less effort than if the finger-receiving recess were absent.

While in the foregoing, I have disclosed an embodiment of the invention in considerable detail for purposes of illustration, it will be understood by those skilled in the art that many of these details may be varied without departing from the spirit and scope of the invention.

We claim:

1. An adhesive faceplate for detachable connection to an ostomy pouch, comprising a thermoplastic pressure ring having a convex bodyside surface and a pouchside surface with an annular mounting rib extending axially therefrom; a coupling ring having a diameter larger than said rib and coaxial therewith; a thin annular web having an inner edge joined to said rib and an outer edge secured to said coupling ring; said pouchside surface of said pressure ring having an annular recess disposed outwardly of said rib and aligned directly with said coupling ring for receiving a user's fingers between said coupling and pressure rings; and a flexible adhesive wafer affixed to said bodyside surface of said pressure ring for adhesive attachment of said faceplate to peristomal skin surfaces.

2. The faceplate of claim 1 in which said pressure ring includes a thin flexible inner connecting portion extending inwardly from said rib and defining a stoma-receiving opening; said wafer having an opening aligned with said opening of said pressure ring and having a bodyside adhesive layer and a pouchside backing layer of stretchable, flexible thermoplastic material; said connecting portion of said pressure ring and said backing layer being welded together in a continuous annular heat seal zone.

3. The faceplate of claim 2 in which said backing layer is formed of porous sheet material and is gas and liquid permeable except in said heat seal zone where the pores thereof are occluded by said weld.

4. The faceplate of claim 3 in which the combined thickness of said flexible backing layer and said inner connecting portion of said pressure ring welded thereto does not exceed about 1.5 mm.

5. The faceplate of claim 2 in which said backing layer is thermoplastic film.

6. The faceplate of claim 2 in which said backing layer is thermoplastic foam.

7. The faceplate of claim 2 in which said pressure ring also has an outer connecting portion extending outwardly beyond said recess; said outer connecting portion and said backing layer being welded together in a continuous heat seal zone.

8. The faceplate of claims 1, 2 or 3 in which said adhesive layer of said wafer comprises a pliant elastomeric adhesive material having particles of one or more hydrocolloids dispersed therein.

* * * * *